US005738664A

United States Patent [19]
Erskine et al.

[11] Patent Number: 5,738,664
[45] Date of Patent: Apr. 14, 1998

[54] SELF-HEALING SEAL FOR USE IN MEDICAL DEVICES

[75] Inventors: Timothy J. Erskine; Kenneth C. Musgrave, both of Sandy, Utah

[73] Assignee: Becton Dickinson and Company, Franklin Lakes, N.J.

[21] Appl. No.: 724,484

[22] Filed: Sep. 30, 1996

[51] Int. Cl.$^6$ .................................. A61M 5/00
[52] U.S. Cl. .................................. 604/256; 604/167
[58] Field of Search .................. 604/158, 164, 604/167, 169, 156, 246, 250, 256

[56] References Cited

U.S. PATENT DOCUMENTS

| | | | |
|---|---|---|---|
| 5,000,745 | 3/1991 | Guest et al. | 604/256 |
| 5,053,014 | 10/1991 | Van Heugten | 604/167 |
| 5,084,023 | 1/1992 | Lemieux | 604/167 |
| 5,104,389 | 4/1992 | Deem et al. | 604/264 |
| 5,407,434 | 4/1995 | Gross | 604/167 |
| 5,460,616 | 10/1995 | Weinstein et al. | 604/167 |
| 5,498,247 | 3/1996 | Brimhall | 604/244 |

FOREIGN PATENT DOCUMENTS 2088215  11/1984  United Kingdom.

Primary Examiner—Corrine M. McDermott
Assistant Examiner—Deborah Blyveis
Attorney, Agent, or Firm—Eric M. Lee

[57] ABSTRACT

A self-healing seal is provided which is particularly adaptable for use in medical applications. The seal includes a housing which defines an interior volume. The housing is formed of a rigid or semi-rigid material such as a rubber or other elastomeric material. A viscous flowable material is disposed within, and substantially fills, the interior chamber of the housing. The viscous flowable material is typically a gel, such as silicone gel. The self-healing seal is configured such that if it is penetrated by an object such as a hypodermic needle, when the needle is subsequently removed, the viscous flowable material flows in such a manner as to fill the space previously occupied by the penetrating object. At the same time the housing is sufficiently elastic to maintain the viscous material within the interior volume of the housing. In this manner a liquid impermeable seal is formed.

5 Claims, 3 Drawing Sheets

5,738,664

SELF-HEALING SEAL FOR USE IN MEDICAL DEVICES

BACKGROUND

1. The Field of the Invention

The present invention relates to a seal for use in medical equipment which is "self-healing." More particularly, the present invention is related to a seal which is designed to be punctured by a catheter, needle, or similar object, but which retains the ability to spontaneously and completely seal upon removal of the penetrating object.

2. Technical Background

In various medical devices it is necessary to provide seals which are substantially impermeable to fluids, but which also allow for hypodermic needles and other similar penetrating implements to penetrate as necessary. Devices of this type include catheter assemblies, respiratory devices, and blood collection systems. It will be appreciated that constructing this type of seal presents a number of unique technical problems.

Specific devices which require this type of seal include various catheters and cannulas (hereinafter "catheters"). These devices are generally placed in fluid communication with a specific part of the body of a patient. For example, catheters are often used to access the vascular system. When this is the case, an introducing needle is generally used to position the catheter within the desired vein or artery. Once the catheter is adequately positioned, the introducing needle is withdrawn from the blood vessel, and is ultimately removed from the catheter device as well. It will be appreciated that it is necessary to maintain a fluid tight seal within the device even after removal of the needle. Thus, the device must include means for closing the opening left as the needle is removed from the device.

Various types of valves or seals have been employed in medical devices of this type. For example, it is conventional to use simple leaf valves in many medical devices in order to provide for selective opening and closing of an access port. In other configurations a luer lock mechanism is placed at the point where the needle or other penetrating implement is removed from the device. Once the implement is removed, a luer lock cap is simply placed over the opening.

This type of device suffers from a number of obvious limitations. When one is dealing with a device filled with liquids, often under significant pressure, leakage will likely occur between the time the needle is removed and the time the cap or other closure means is put into position. This increases the likelihood of contamination of the catheter system, as well as contamination of the surrounding work environment by blood or other bodily fluids.

Another alternative is to place a relatively rigid elastomeric plug in the end of the device through which the penetrating implement passes. The plug is generally constructed of a relatively rigid rubber material. These devices are designed such that they automatically seal when the needle or other implement is removed.

One problem with this type of device is the friction between the needle and rubber plug. In order to provide for an adequate seal it is necessary to compress the plug. This makes movement of the needle through the plug more difficult. In addition, the need to exert pressure on the plug limits the choices of materials usable in constructing a suitable housing. The result is that often times these devices are not particularly compatible with the skin of the patient, particularly when it is necessary for the device to be next to the skin over an extended period of time. This may lead to irritation, possible infection, and related problems.

Thus, there is a need for an alternative seal for use in the contexts mentioned above. In that regard, it would be an advancement in the art to provide an improved barrier or seal which was capable of closing openings left by needles and other similar implements. It would also be an advancement in the art to provide such a device which could be constructed from a wide variety of materials, including materials which are more compatible with the skin of patients than those materials presently in use. In addition, it would be an advancement in the art to provide such a seal that was adaptable of use in a variety of different devices and which is very reliable.

Such apparatus are disclosed and claimed herein.

BRIEF SUMMARY AND OBJECTS OF THE INVENTION

The present invention is related to a self-healing seal for use in various medical devices, particularly devices such as catheter assemblies where it is important to maintain a fluid seal while performing a series of manipulation steps. The seal of the present invention includes a form-retaining housing which forms the exterior of the device. The form-retaining housing defines an interior chamber. Placed within the interior chamber is a bolus of viscous flowable material. Generally, sufficient viscous flowable material will be placed within the interior chamber of the housing such that the chamber is substantially filled.

The seal is specifically configured such that if it is penetrated by a penetrating implement, such as a hypodermic needle, and the object is subsequently removed, the viscous flowable material flows to fill the space previously occupied by the penetrating object. At the same time the housing is sufficiently elastic to maintain the viscous material within the interior chamber once the needle is removed. In this manner a liquid impermeable seal is provided.

One significant feature of the present invention is that the housing may be constructed of a wide range of materials. Because of the fact that the housing is not required to place a high level of pressure on the interior material, it is possible to select from a wider variety of materials. Among the possible material candidates are those which are compatible with the skin of a patient. Accordingly, it is possible to design the device such that it does not irritate the patient. Examples of usable materials include rubbers and synthetic elastomers such as latex, polyisoprene, silicone, and polyurethanes.

Various flowable viscous materials can also be used. For example, gels such as silicone gels are suitable and are within the scope of the present invention. It is possible to select gels which increase viscosity or solidify upon contact with oxygen, water or other substances in order to assure a complete seal.

The present invention is also advantageous in that it is possible to lower the friction on the needle as it is withdrawn from the device. In existing systems, high levels of friction on the needle are often a drawback, and may even result in the plug or seal being inadvertently dislodged or relocated. Thus, the present invention provides a significant advantage in that the needle is able to slide smoothly through the seal.

These and other advantages of the invention will become apparent upon reading the following detailed description and appended claims, and upon reference to the accompanying drawings.

BRIEF DESCRIPTION OF THE DRAWINGS

In order to more fully understand the invention, a more particular description of the invention will be rendered by

Figure 1:
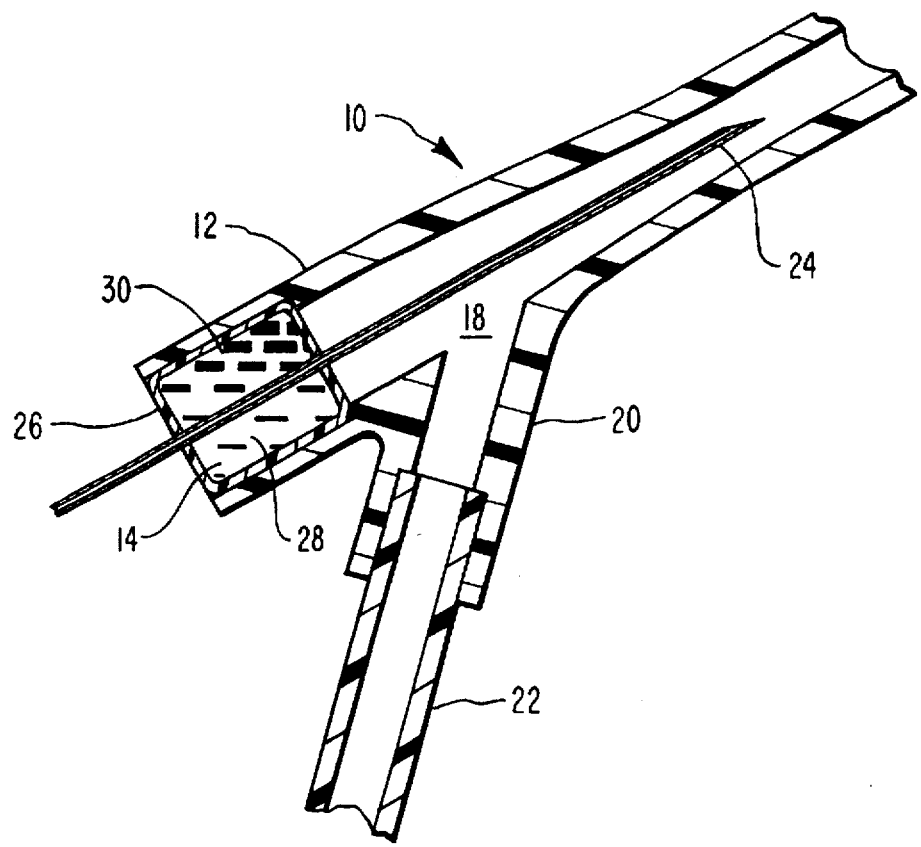

3 reference to specific embodiments which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1 is a cross sectional view of a catheter assembly employing the present invention.

Figure 2:
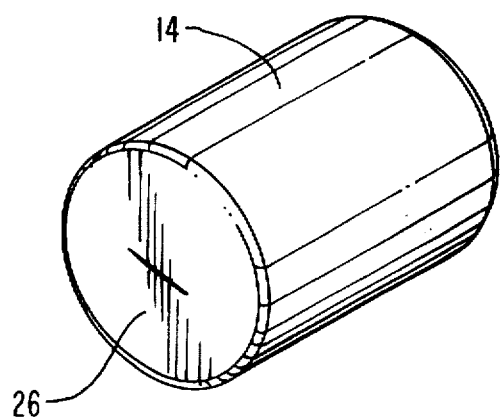

FIG. 2 is a perspective view of the present invention illustrating specifically the form-retaining housing.

Figure 3:
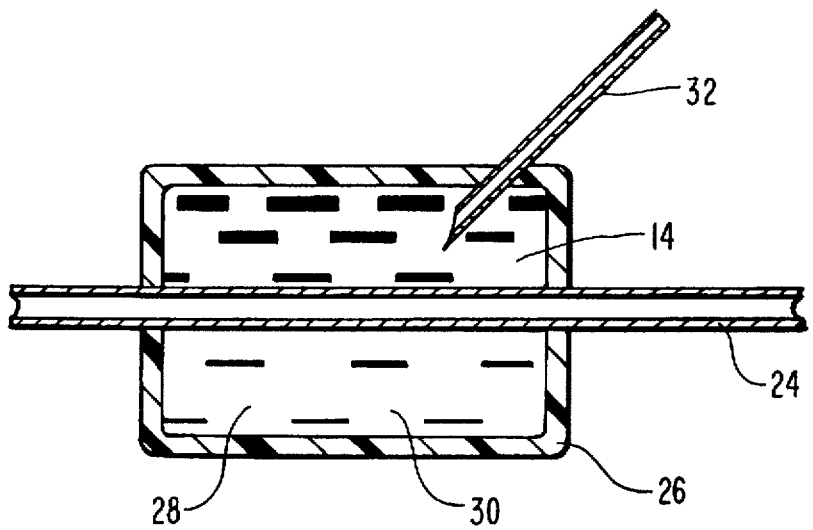

FIG. 3 illustrates the manner in which one embodiment of the present invention is manufactured with a needle in place and penetrating the housing.

Figure 4:
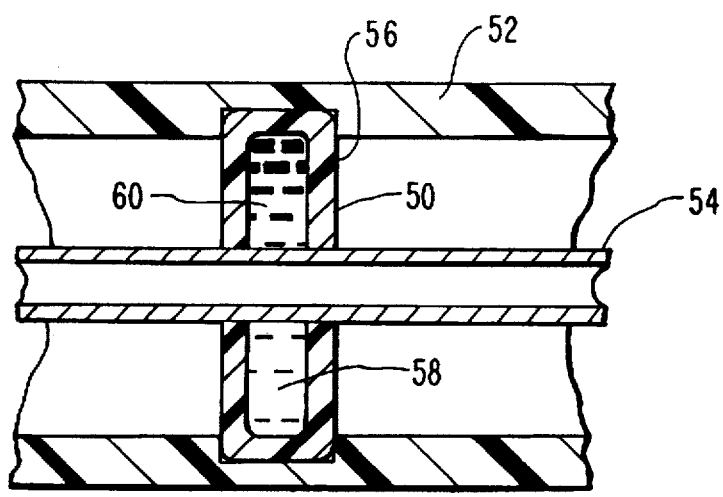

FIG. 4 is a cross-sectional view of an alternative generally disk-shaped embodiment of the present invention.

Figure 5:
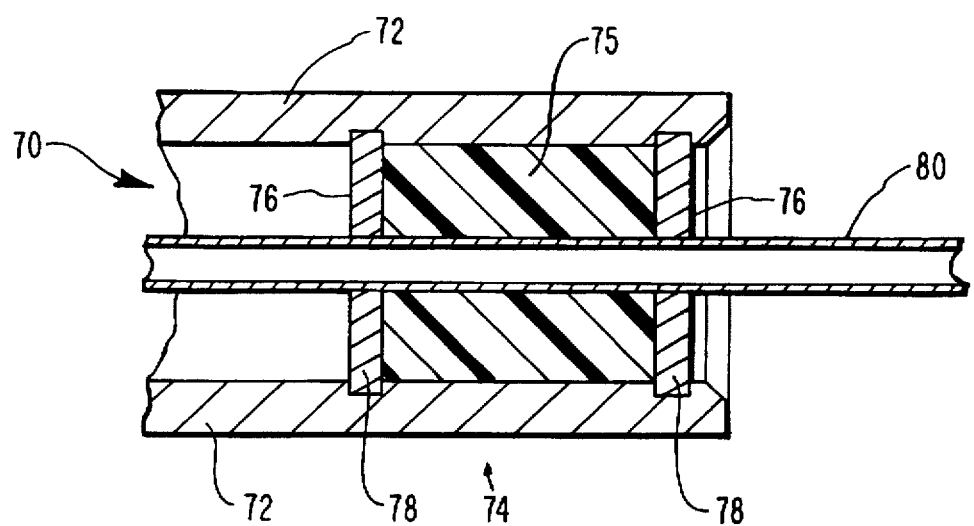

FIG. 5 is a cross-sectional view of a farther alternative embodiment wherein the catheter body forms a portion of the seal.

DETAILED DESCRIPTION OF THE PREFERRED EMBODIMENTS

The present invention can be best understood by reference to the drawings where like parts are designated with like numerals throughout. A portion of a typical catheter assembly is generally designated 10 in FIG. 1. Disposed within the structure 12 of the catheter assembly 10 is one representative embodiment of the self-healing seal 14 of the present invention.

In the present embodiment, a catheter (not shown) provides access to a vein or artery such that blood can be withdrawn from a patient or such that necessary fluids can be provided to the patient. In either case, the fluids flow through a Y-shaped section 18 into an inlet 20. The inlet 20 is in turn connected to a tube 22 through which intravenous fluids are provided to the patient, or through which blood is collected from the patient.

As mentioned above, catheters of this type are typically positioned by means of an introducing needle 24. The introducing needle 24 is used to locate and penetrate the desired vein or artery. Once the introducing needle is in position, it is used to position the catheter in the same vein or artery. After the catheter is in the desired position, the introducing needle 24 is withdrawn from the vein or artery and is ultimately withdrawn from the catheter assembly 10 as well. In the embodiment of the invention as illustrated in FIG. 1, when the introducing needle is withdrawn it is pulled through and removed by way of the self-sealing seal 14.

As illustrated in FIG. 1, the seal 14 includes a form-retaining housing 26. As mentioned above, the housing 26 may be constructed of a wide variety of materials. Examples of such materials include latex, polyisoprene, silicone, and various polyurethanes. The housing 26 is configured such that it fits securely within the catheter structure 12 and such that it forms an interior chamber 28. The interior chamber 28 is, in turn, substantially filled with a flowable viscous material 30 such as a gel. Silicone gel is one presently preferred material.

It will be appreciated that as the introducing needle 24 is withdrawn from the catheter assembly 10, it would tend to leave an opening in the seal 14 because it is held in a deformed state by the presence of the penetrating object and stored before use for up to five years, the material takes on a "compression set." However, because of the design of the present invention, the opening that would otherwise be left is self-sealed. That is, the elastomeric nature of the form-retaining housing 26 causes it to substantially close. At the same time, the viscous material 30 is fluid enough to fill the void left by the introducing needle, but viscous enough that the viscous material 30 cannot flow through the opening.

FIG. 2 illustrates the self-healing seal 14 as illustrated in FIG. 1. As illustrated in FIG. 2, the introducing needle has been withdrawn from the seal 14. Yet, the viscous material is held in place within the housing 26 due to the elastic nature of the housing 26. In the interior of the seal 14, the viscous material (not shown) will have flowed sufficiently to fill the path of the needle and to complete the seal. As illustrated in FIG. 2, the seal 14 is generally cylindrical in shape. However, it is possible to adapt the seal to other shapes, sizes, and configurations.

FIG. 3 illustrates one method of forming the self-healing seal 14 of the present invention. As illustrated in FIG. 3, the introducing needle 24 is initially inserted through the housing 26. Once this has been accomplished, a second needle 32 is inserted through the wall of the housing 26 and into the interior chamber 28. The interior chamber 28 of the housing 26 is then substantially filled with a flowable viscous material 30, such as a gel. Once the introduction of the gel 30 into the interior chamber 28 is completed, the needle 32 is removed. Because of the self-healing properties of the seal 14, the gel remains in place even after the needle 32 has been removed.

Once the introducing needle 24 has been position within the seal 14, and the seal 14 inflated with gel 30, the device is ready for use. As described above with reference to FIG. 1, the device can then be positioned within a catheter structure 12. While the introducing needle 24 could be inserted into the device after the device is inflated with gel 30 and placed within the catheter structure 12, this is not generally preferred. The procedure described above is generally preferred in order to assure that the introducing needle 24 does not become clogged with gel prior to use.

FIG. 4 illustrates a further embodiment of the device of the present invention. The self-healing seal 50 illustrated in FIG. 4 is somewhat more disk-shaped than the seal 14 described above. The seal 50 is illustrated positioned within a catheter 52. A penetrating object 54, such as a needle, is illustrated passing through the seal 50. As with the previously described embodiment, the seal 50 illustrated in FIG. 4 comprises a form retaining housing 56 which defines an interior volume 58. Placed within the interior chamber 58 is a gel 60 or other flowable material.

Referring now to FIG. 5, a further embodiment of the present invention is illustrated and generally designed 70. In this embodiment of the device the wall 72 of the catheter 74 forms a portion of the seal. As illustrated in FIG. 5 a pair of disks 76 are fitted within grooves 78 within the interior wall 72 of catheter 74. Together the disks contain a gel 75. As discussed with respect to the previously described embodiments, one or both of the disks 76 is formed of a generally elastomeric material which substantially closes after the penetrating object, such as needle 80 is removed. If only one of the disks 76 is elastomeric in nature, the other disk is likely constructed of a rigid material having a close clearance for the penetrating object. In any event, those of skill in the art will appreciate that various combinations of materials may be employed to achieve the objectives of this particular embodiment of the invention. As with the previously described embodiments, the interior of the space defined by wall 72 and the pair of disks 76 is filled with a gel material. Thus, in this embodiment of the invention it is possible to achieve the advantages of a seal healing seal without the necessity of a complete housing for the gel in that the catheter 74 provides a portion of the required housing.

Thus, the present invention accomplishes the objectives identified above. The device of the present invention provides a seal which self-heals when a penetrating object is removed through the seal. The device is capable of lowering the friction that would otherwise be experienced in removing the penetrating object through the seal. The seal is also very reliable. The seal self-heals such that there is no need for medical personnel to be concerned with closing the seal once the penetrating object is removed. This makes use of catheters and other similar devices easier and safer.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by Letters Patent is:

1. A medical device, comprising:

a housing defining an interior portion and a distal groove and a proximal groove axially spaced from one another within the interior portion;

a distal disk disposed in the distal groove;

a proximal disk disposed in the proximal groove; and a viscous flowable material disposed within the interior portion between the distal disk and the proximal disk.

2. The medical device of claim 1 wherein the viscous flowable material is a gel.

3. The medical device of claim 2 wherein the gel is a silicone gel.

4. The medical device of claim 1 wherein one of the distal disk or the proximal disk is formed of a rubber material.

5. The medical device of claim 1 wherein one of the distal disk or the proximal disk is formed of a polymeric elastomeric material.

* * * * *